(12) United States Patent
Marty et al.

(10) Patent No.: US 9,746,487 B2
(45) Date of Patent: Aug. 29, 2017

(54) DEVICE FOR STORING OF FLUID CONTAINERS

(71) Applicant: Roche Diagnostics Operations, Inc., Indianapolis, IN (US)

(72) Inventors: Christian Marty, Goldau (CH); Beat Rene Widmer, Steinhausen (CH); Markus Jeziorski, Meierskappel (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/960,719

(22) Filed: Dec. 7, 2015

(65) Prior Publication Data

US 2016/0169926 A1    Jun. 16, 2016

(30) Foreign Application Priority Data

Dec. 13, 2014  (EP) ..................................... 14197837

(51) Int. Cl.
  *G01N 35/10*  (2006.01)
  *G01N 35/00*  (2006.01)
  *G01N 35/04*  (2006.01)

(52) U.S. Cl.
  CPC ..... *G01N 35/1011* (2013.01); *G01N 35/0099* (2013.01); *G01N 35/04* (2013.01); *G01N 35/1081* (2013.01); *G01N 2035/00089* (2013.01); *G01N 2035/00287* (2013.01); *G01N 2035/00326* (2013.01); *G01N 2035/0403* (2013.01); *G01N 2035/0427* (2013.01); *G01N 2035/1051* (2013.01)

(58) Field of Classification Search
  None
  See application file for complete search history.

(56) References Cited

U.S. PATENT DOCUMENTS 5,171,530 A * 12/1992 Pennatto ................... B01L 9/06
                                                        422/63
5,333,717 A   8/1994 Rosenberg et al.
5,462,715 A * 10/1995 Koch ..................... G01N 35/04
                                                       422/549

(Continued)

FOREIGN PATENT DOCUMENTS

EP        2333563 A1    6/2011
JP    2005-061897 A     3/2005

*Primary Examiner* — Sean E Conley
*Assistant Examiner* — Benjamin R Whatley
(74) *Attorney, Agent, or Firm* — Roche Diagnostics Operations, Inc.

(57) ABSTRACT

A device for container storing is presented. The device comprises storage with at least one storing level including a pipetting storing level for fluid pipetting. Each storing level has storing positions having a container holder to detachably hold at least one container. A handler is movable with respect to the storage for transferring containers with respect to the storing positions. A storing position of the pipetting storing level includes a flat spring to bias a container against the container holder. The flat spring has a through hole to provide a pipette access to a lid of the container. A system for pipetting is also presented, comprising the device and a pipettor movable with respect to the pipetting storing level with at least one pipette for pipetting contained in a container stored in the pipetting storing level. The pipette has a pipette tip to penetrate a lid of the container.

12 Claims, 7 Drawing Sheets

(56) References Cited

U.S. PATENT DOCUMENTS

| | | | |
|---|---|---|---|
| 6,270,726 B1 | 8/2001 | Tyberg et al. | |
| 2006/0204997 A1 | 9/2006 | Macioszek et al. | |
| 2010/0132484 A1* | 6/2010 | Schacher | G01N 35/1002 |
| | | | 73/863.01 |
| 2012/0251275 A1 | 10/2012 | Malin | |
| 2012/0301359 A1* | 11/2012 | Kraemer | G01N 35/04 |
| | | | 422/64 |
| 2013/0130369 A1* | 5/2013 | Wilson | B01L 3/5085 |
| | | | 435/289.1 |
| 2013/0137110 A1 | 5/2013 | Kraihanzel | |
| 2014/0286124 A1 | 9/2014 | Donohue et al. | |
| 2015/0274423 A1* | 10/2015 | Borodkin | B65G 1/137 |
| | | | 700/218 |

\* cited by examiner

DEVICE FOR STORING OF FLUID CONTAINERS

CROSS-REFERENCE TO RELATED APPLICATIONS

This application claims priority to EP 14197837.9, filed Dec. 13, 2014, which is hereby incorporated by reference.

BACKGROUND

The present disclosure generally relates to the field of analytical sample processing and, in particular, relates to a device for the storing of fluid containers and a system for pipetting of fluids comprising such storing device.

In automated clinical analyzers, liquid samples, such as, for example, bodily fluids, can be tested by various diagnostic methods. Since there is a strong demand for offering a wide variety of analytical functions and with a view to improve effectiveness in sample processing, modern analyzers often process samples with high throughput. As a result, modern analyzers are subject to an elevated consumption of reagents which may be satisfied by either preloading the analyzer with an adequate number of reagent containers or performing frequent manual reloading operations. In the first case, while analyzers can be used in a comfortable stand-alone mode, a larger number of reagent containers require much storage space which increases the overall dimensions of the analyzer. In the latter case, while analyzers can be made small and compact, frequent reloading operations are required. In view of an increasing tendency to install small and compact analyzers, a convenient trade-off between the number of stored reagent containers and the frequency of manual reloading operations when operating the analyzer in daily routine has to be found. Consequently, modern clinical analyzers often have supplemental storage space for reagent container.

In modern analyzers, automated sample processing often involves the transfer of precise amounts of reagents to the samples by pipettes. In a typical pipetting operation, a pipette is lowered into a reagent container until the pipette tip dips into the reagent and can be sucked in, followed by lifting the pipette and moving the pipette to a position enabling the addition of the reagent to a sample. In order to provide the pipette free access to the reagent, the reagent container which normally is closed by a container lid is opened by removing the lid from a container opening or the pipette tip is inserted through the lid. Due to the fact that removal of the lid needs extra-time and the reagent is exposed to ambient air until the container is closed again, it often is desirable to penetrate the lid by the pipette tip. However, in automated pipetting operations, when the pipette is drawn out of the reagent container, the reagent container is likely to be raised due to a frictional force arising between the upwards moved pipette tip and the lid. Consequently, the position of the reagent container can be changed so that further pipetting operations may be impeded or even a crash between the pipette and the reagent container can be caused.

Therefore, there is a need for a device for storing fluid containers which enables a high-throughput processing of samples without a need to frequently reload fresh reagent containers and further ensures safe and reliable pipetting of reagents.

SUMMARY

According to the present disclosure, a system and a device for storing of fluid containers is presented. The device can comprise at least one storage provided with one or more storing levels including a pipetting storing level adapted for pipetting of fluids, each storing level having a plurality of storing positions, each of which having a container holder adapted to detachably hold at least one fluid container; and a handler movable with respect to the storage adapted for automatically transferring fluid containers at least with respect to the storing positions. A storing position of the pipetting storing level can include a flat spring arranged to bias a fluid container against the container holder, with the flat spring provided with at least one through-hole positioned to provide a pipette access to a container lid of the fluid container.

In accordance with one embodiment of the present disclosure, the system can comprise a pipettor movable at least with respect to the pipetting storing level provided with at least one pipette for pipetting of fluid contained in a fluid container stored in the pipetting storing level, wherein the pipette has a pipette tip configured to penetrate a lid of the fluid container Accordingly, it is a feature of the embodiments of the present disclosure to provide a system and a device for storing fluid containers which enables a high-throughput processing of samples without a need to frequently reload fresh reagent containers and further ensures safe and reliable pipetting of reagents. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

In the following description, reference is made to first to third directions (x, y, z), perpendicularly aligned with respect to each other, with the first and second directions (x, y) spanning a plane and the third direction (z) being perpendicularly aligned with respect to the plane. In one embodiment, the first and second directions (x, y) can span a horizontal plane and the third direction (z) can be vertically aligned to the plane (direction of fall).

As used herein, the term "fluid container" can relate to any vessel having at least one compartment for containing fluid such as, but not limited to, a reagent for processing samples. Specifically, the fluid container can have plural separate compartments, e.g. aligned in a row, containing fluids which can be similar or different with respect to each other. Each fluid compartment can be closed by a lid configured to be penetrated by a pipette tip such as, but not limited to, a metallic needle, in the following denoted as "penetrable lid". Specifically, in one embodiment, the fluid container can comprise one or more fluid compartments, each of which is closed by a lid, with the lid comprising a pierceable material, e.g. an elastomeric material such as a rubber septum. The lid may comprise a depression at an upper side.

A device for storing of fluid containers, in the following also referred to as "device" is presented. The device can comprise storage having a plurality of storing positions adapted for storing fluid containers such as, but not limited to, reagent containers. Specifically, the storage can be provided with one or more storing levels, each of which can extend in a plane spanned by a first direction and a second direction with the first direction orthogonal to the second direction. One or more storing levels can be stacked in a third direction with the third direction orthogonal to the first and second directions. Each storing level may, for instance, extend in a horizontal plane with two or more storing levels being stacked in vertical relationship with respect to each other. Furthermore, the storage can include a storing level configured for pipetting of fluids contained in at least one fluid container stored therein, in the following referred to as "pipetting storing level". In one embodiment, the pipetting storing level can be an uppermost (highest) storing level of the storage right on top of the other storing levels.

Each storing level can have a plurality of storing positions, each of which is adapted to store at least one fluid container, with the storing positions arranged in a one- or two-dimensional array. Accordingly, in each storing level, fluid containers can be serially arranged with respect to each other in one or more rows. In one embodiment, each row can extend in the first direction with the rows arranged one after another along the second direction. Specifically, each storing position can comprise a container holder adapted to detachably hold at least one fluid container. The storage can be considered as fluid container rack.

The storing device can further include a handler movable at least with respect to the storage and adapted to automatically handle (manipulate) fluid containers at least with respect to the storing positions so that each fluid container can be transferred from one storing position to another.

According to one embodiment, a storing position of the pipetting storing level can comprise a flat spring (leaf spring) arranged to bias a fluid container against the container holder, that is to say, to force the fluid container against the container holder by the resilient force generated by the flat spring. In one embodiment, the flat spring can be arranged to force the fluid container in the same direction as one or more pipettes can be moved away from the fluid container, e.g., in the third direction (e.g. vertical direction). In one embodiment, the flat spring can be arranged to contact an upper side of a fluid container in the storing position with the upper side of the fluid container, depending on the number of fluid compartments, provided with one or more penetrable lids. Specifically, the flat spring can be provided with at least one through-hole positioned to provide a pipette access to a penetrable lid of a fluid container.

Accordingly, due to a compact packing of the fluid containers, the device may advantageously be made compact without requiring frequent reloading operations for refilling of fresh fluid containers even in case of a comparably high consumption of reagent in processing liquid samples. Furthermore, each fluid container in the pipetting storing level can reliably be secured in the storing position by being pressed against the container holder by the resilient force of the flat spring so that the fluid container can be reliably kept in place when performing a pipetting operation, in particular, when pulling the pipetting tip penetrating the lid out of the fluid container.

In one embodiment, each flat spring can comprise a plurality of through-holes, with the through-holes positioned to provide one or more pipettes access to a corresponding number of penetrable lids of one fluid container. Fluids may simultaneously be pipetted with respect to plural fluid compartments of a fluid container in order to increase speed and efficiency of sample processing. In one embodiment, a plurality of flat springs can be formed by a one-piece element, such as, for example, a steel sheet. Manufacturing and installation can thereby be facilitated.

In one embodiment, the device can comprise a device housing and the one or more through-holes of each flat spring can be positioned in correspondence to holes of the device housing to provide access for one or more pipettes to one or more penetrable lids of a fluid container from outside the device housing. Accordingly, on the one hand, the storage can be separated from the surroundings so as to obtain an at least partially closed storing space protecting the fluids contained in the fluid containers and enabling cooling of the fluids. On the other hand, pipetting operations with respect to fluid containers stored in the pipetting storing level can be performed without a need to remove the fluid containers from the storage.

In one embodiment, the handler can comprise a lug configured to engage with the flat spring of a storing position in a manner to act against the resilient force of the flat spring when the handler is in a transfer position for transferring a fluid container to or away from the storing position. Accordingly, the fluid container can readily be put in or removed from a storing position without a need to use a further device for counter-acting the resilient force of the flat spring to provide access to the storing position. As a result, because the handler has a double function, material and costs for manufacturing the device can advantageously be saved.

In one embodiment, the flat spring can have a curved shape, e.g. upwardly or downwardly bent with respect to a fluid container held in the storing position so as to form at least one contact portion. The flat spring can be configured so that the at least one contact portion can directly contact a fluid container secured by the flat spring in holding position. The contact portion can protrude towards the fluid container (e.g. an upper side thereof). Furthermore, the lug of the handler can be configured to engage the flat spring to act against the resilient force of the flat spring when the handler is moved in or kept in a transfer position for transferring a fluid container to or away from the storing position, can readily be engaged with the flat spring protruding from the upper side of the fluid container.

In one embodiment, a free-ending end portion of the flat spring can protrude from the storing position (towards the handler in a transfer position for transferring a fluid container to or away from the storing position) for engagement with the lug of the handler. Accordingly, the lug of the handler can easily and reliably be brought in engagement with the flat spring.

In one embodiment, the container holder of a storing position can comprise a projection configured to be brought in fitting engagement with a fluid container in the storing position so as to block movement of the fluid container relative to a transfer direction for transferring the fluid container to or away from the storing position by the handler. Accordingly, the fluid container can be secured by the container holder relative to the transfer direction. As a result, together with the resilient force of the flat spring pressing the fluid container against the container holder, the fluid container can reliably be secured in the storing position.

In one embodiment, the storing device can have a function of cold-storage, that is to say, can be operable to cool the fluid containers in their storage positions. Specifically, due to the highly-dense packaging of the fluid containers, efficient cooling of the fluid containers may advantageously be performed. Moreover, fluid containers can be continuously cooled in the pipetting storing level so that cooling of fluids may be possible even during and in-between pipetting operations so that the on-board stability of the fluids can be extended.

In one embodiment, the storing device can include two storages respectively provided with storing positions for storing of fluid containers arranged in opposite relationship with respect to each other with the handler arranged in-between the storages for automatically transferring the fluid containers at least with respect to the storing positions of both storages. Such embodiment can advantageously allow for highly-dense packing of fluid containers without a need to provide for individual handlers for handling the fluid containers which advantageously can allow saving constructional space and costs. Furthermore, due to two pipetting storing levels, the number of pipetting operations can advantageously be increased to make the processing of samples faster and more efficient.

In one embodiment, the storage can be made up of a plurality of modular sub-storages which may be added to or removed from the storage. Such embodiment can advantageously allow for readily adapting the size of the storage to the specific needs of the user and/or the size of the system.

In one embodiment, the device can further comprise a controller for controlling the handler for handling fluid containers contained in the storage of the storing and handling device.

In one embodiment, the storing device can be a modular device. As used herein, the term "modular" can describe a structural entity which can be used and changed as one component of a larger system for pipetting fluids or processing samples.

The invention proposes a new system for pipetting of fluids, in the following referred to as "system", comprising at least one storing device as above-described which can be particularly useful for the automated processing of samples involving adding of fluid such as reagents to the samples. The system can further comprise at least one pipetting device, in the following referred to as "pipettor", movable at least with respect to the pipetting storing level. Specifically, the pipettor can comprise at least one pipette adapted to pipette fluids contained in fluid containers stored in the pipetting storing level. The pipette can have a pipette tip configured to penetrate a (penetrable) lid of a fluid container such as, but not limited to, a metallic needle. The pipettor can be configured in such a manner that the one or more pipettes can be moved towards and away from a fluid container stored in the pipetting storing level. In one embodiment, the one or more pipettes can be lowered and lifted along the third direction (e.g. vertical direction).

The storing device may be configured as integrated component of the system for pipetting of liquids but can also be a modular component thereof which can advantageously make it possible to be readily adapted to various system sizes. The modular storing device can, e.g., have a module (device) housing surrounding the storage and handler so as to separate its components from other system components, e.g., for facilitating maintenance work.

Figure 1:
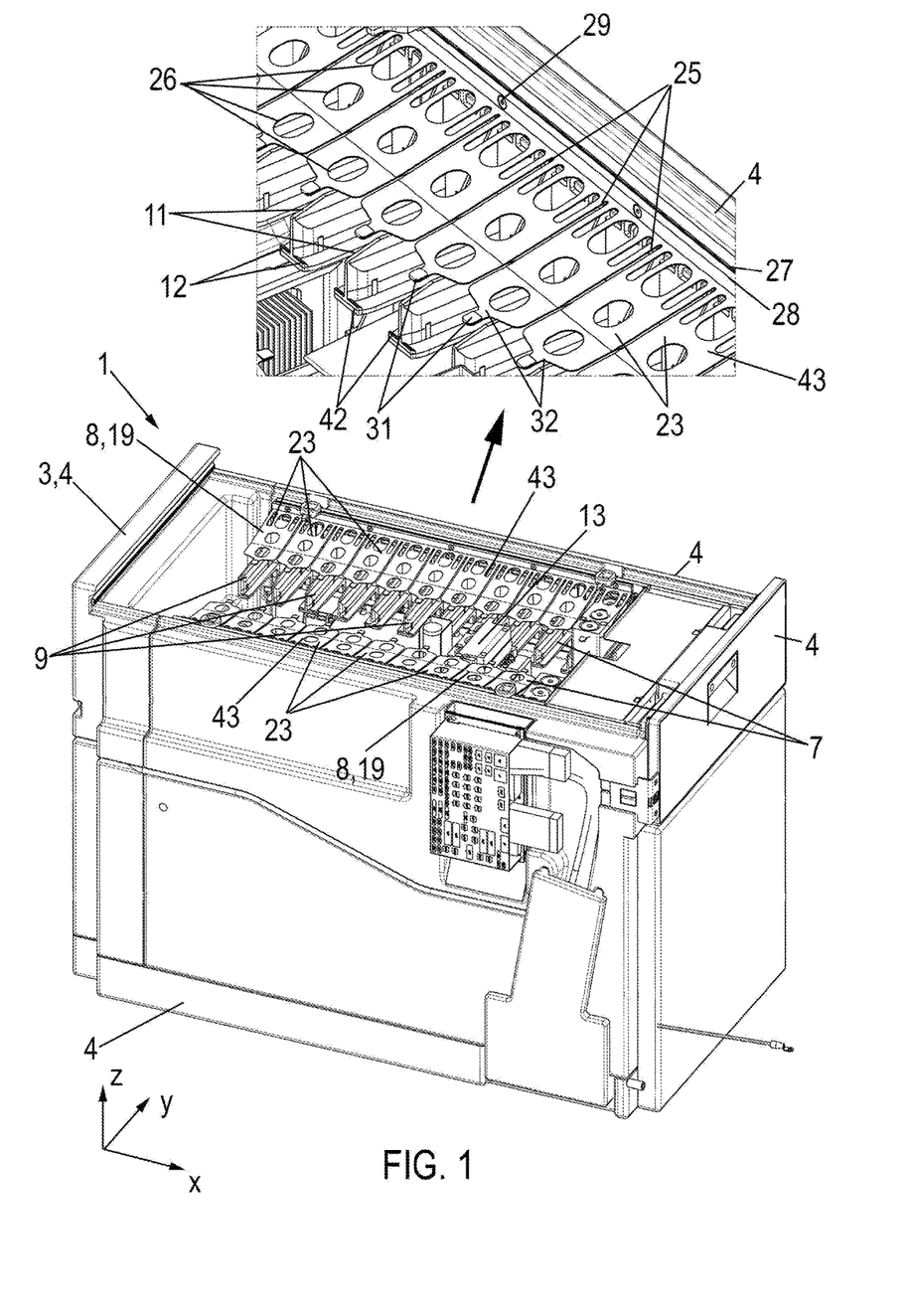
FIG. 1 illustrates a perspective view and an enlarged detail of the device for storing of fluid containers according to an embodiment of the present disclosure.

Referring initially to FIG. 1, an automated system for pipetting fluids, generally referred to under reference numeral 100, is explained. The system 100 can be part of a clinical analyzer (e.g. chemical and/or immunochemical analyzer) for analyzing of liquid samples in order to determine the presence/amount or absence of specific substances in the liquid samples.

Figure 2:
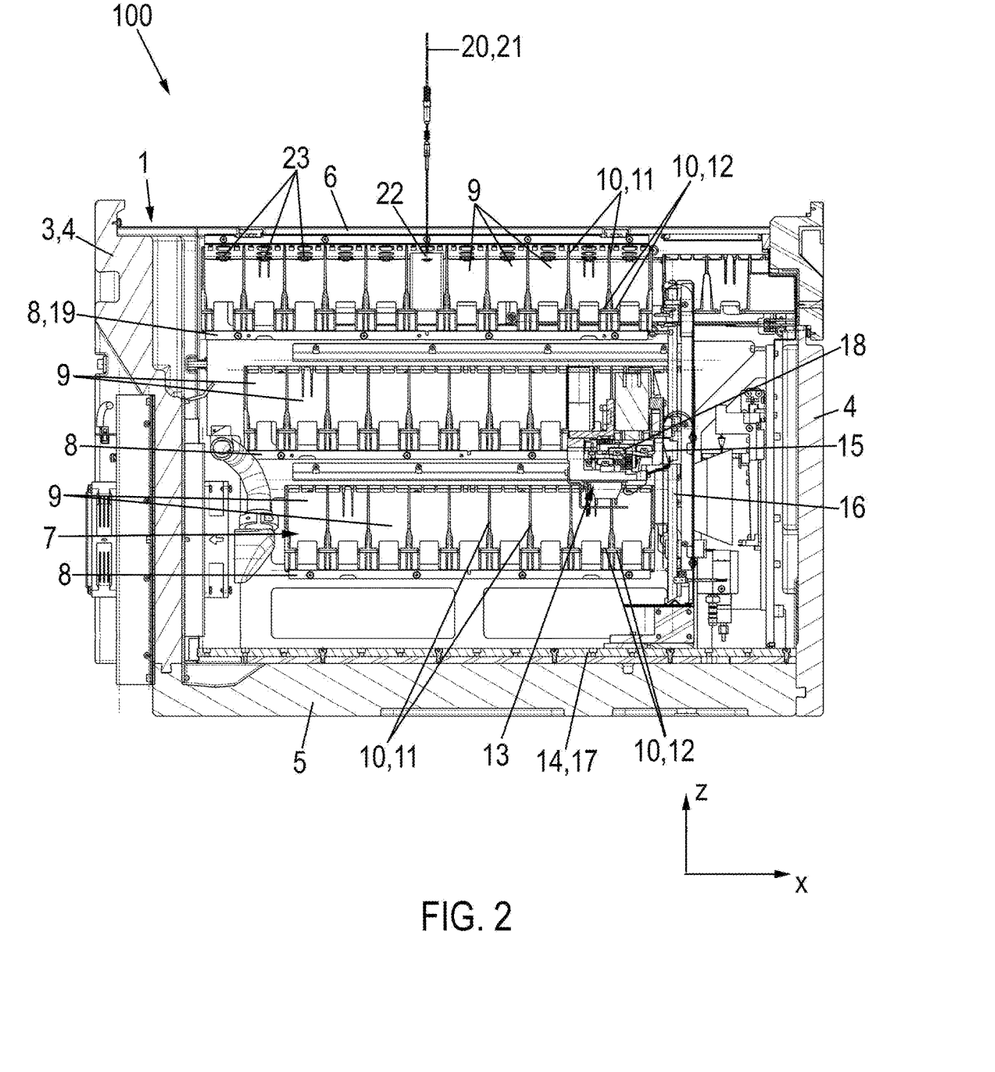
FIG. 2 illustrates a sectional view of the device of FIG. 1 according to an embodiment of the present disclosure.

With particular reference to FIGS. 1 and 2, the system 100 can includes an automated device 1 for storing and handling of fluid containers 2 containing fluids such as, for example, reagents for mixing with liquid samples. In one embodiment, the storing device 1 can be configured as a functional and structural entity enclosed by a device housing 3 comprised of four housing side walls 4, a housing top wall 6 and a housing bottom wall 5 which together can form an interior space for accommodating the various device components.

As illustrated in FIG. 1, in one embodiment, the storing device 1 can comprise two racks 7 (i.e., storage) for storing of the fluid containers 2. The two racks 7 can be arranged in opposite relationship with respect to each other so as to be distanced in y-direction with each rack 7 being, for example, fixed to a housing side wall 4. As illustrated in FIG. 2, in one embodiment, each rack 7 can have a plurality of rack levels 8 (i.e., storing levels) positioned one upon the other in vertical z-direction. In one embodiment, each rack level 8 can be a modular rack component which, for instance, can be detachably fixed to the housing side wall 4 allowing each of the individual rack levels 8 to be added to or removed from the rack 7 as desired. In one embodiment, each rack 7 can be provided with number of three rack levels 8 vertically stacked one upon the other. It, however, is to be understood, that a larger or smaller number of rack levels 8 can be envisaged according to the specific demands of the user.

Each rack level 8 can offer a plurality of storing positions 9, each having a box-like container holder 10 for holding e.g. one fluid container 2. In one embodiment, each container holder 10 can be configured to hold more than one fluid container 2. In another embodiment, the storing positions 9 can be serially arranged with respect to each other in horizontal x-direction.

In one embodiment, the container holders 10 can be formed by holder side plates 11, each of which can extend in y- and z-direction, with two holder bottom plates 12, each of which can extend in x- and y-direction projecting away at right angles from each holder side plate 11. Two adjacent holder side plates 11 and two holder bottom plates 12 facing each other together can form one container holder 10 for receiving one fluid container 2. A fluid container 2 can be placed on the holder bottom plates 12 and can be kept in upright position between the holder side plates 11. Here, the container holders 10 may not be adapted to secure the fluid containers 2 in vertical direction which can advantageously enable the use of fluid containers 2 which may not be adapted to the container holders 10 except for the dimensions of the fluid containers 2. In the racks 7, the fluid containers 2 can be densely packed. Voids in-between adjacent fluid containers 2 can be made rather small or may even disappear as long as frictional forces allow for slidably moving the fluid containers 2 in and out of the container holders 10. Similarly, the distance in z-direction between adjacent rack levels 8 can be made small in appropriately choosing a vertical distance between the rack levels 8 in accordance with a vertical height of the fluid containers 2.

The storing device 1 can further include a handler 13 for handling (manipulating) the fluid containers 2 with respect to the storing positions 9 arranged in-between the two racks 7. In one embodiment, the handler 13 can comprise a positioning device 14 for positioning a transfer head 15 in two directions of travel (x-direction and z-direction) by a two-rail translation mechanism. The two-rail translation mechanism can comprise a first rail 16 extending in z-direction for guiding the transfer head 15 in z-direction and a second rail 17 extending in x-direction for guiding the first rail 16. Accordingly, the transfer head 15 can be freely moved along the y- and z-direction so as to position the handler 13 in a plane spanned by the y- and z-direction with the transfer head 15 facing a storing position 9 and in which a fluid container 2 can be moved in or away from the storing position 9, in the following denoted as "transfer position". The two-rail translation mechanism can, e.g., be driven by a belt-drive coupled to two electric motors which is well-known in the art and, thus, need not be further elucidated herein.

The transfer head 15 can be configured to transport at least one fluid container 2 and can be provided with a fluid container transfer mechanism 18 adapted for moving a fluid container 2 transported by the transfer head 15 to a storing position 9 or to move a fluid container 2 away from a storing position 9 with the transfer head 15 being brought in a transfer position. In one embodiment, the transfer mechanism 18 can comprise a push/pull element which can be moved by the transfer head 15 between the holder bottom plates 12 and which can be brought in engagement with the bottom of a fluid container 2 to move the fluid container 2 to the storing position 9 and can also be brought in gripping engagement with a fluid container 2 in a storing position 9 to move the fluid container 2 to the transfer head 15. Accordingly, a fluid container 2 may be arbitrarily placed in any container holder 10 in a storing position 9 or removed therefrom by the handler 13.

In one embodiment, the storing device 1 can further include at least one input/output position which, being similar in construction to the storing positions 9 enabling manipulation by the handler 13, can allow for a manual or automated loading/unloading of fluid containers 2. In one embodiment, each fluid container 2 can bear a machine-readable label which can be automatically read by a reader so as to provide inventory information of the racks 7. Each label on a fluid container 2 may, for instance, code for a lot number or any other information suitable for identifying the fluid container 2. It may also contain additional information such as use-by date which may be relevant for use of the reagents contained. The reader can, e.g., fixed to the transfer head 15.

In the system 100, in one embodiment, the interior space of the device 1 can be a cold-storage configured to cool the stored fluid containers 2. Specifically, cooling of the interior space can, for instance, be effected by circulating cooling-air. Due to the highly-dense packing of the fluid containers 2, cooling can be highly efficient.

As illustrated in FIGS. 1 and 2, in one embodiment, each rack 7 can have an upmost rack level 8 in which each storing position 9 can be configured to pipette fluids contained in fluid containers 2 stored therein, in the following denoted as "pipetting rack level 19". Each storing position 9 of the pipetting rack level 19 can comprise a flat spring (leaf spring) 23 arranged to bias a fluid container 2 against the container holder 10. Specifically, with particular reference to FIGS. 3 and 4, in one embodiment, the flat spring 23 can be arranged to sandwich a fluid container 2 between the flat spring 23 and the container holder 10 so as to force the fluid container 2 against the container holder 10 by the resilient force (biasing force) generated by the flat spring 23. In one embodiment, the flat spring 23 can force the fluid container 2 against the holder bottom plates 12 of the container holder 10. Accordingly, with particular reference to FIG. 4, in each storing position 9, a fluid container 2 can be inserted between the flat spring 23 and the container 10 when transferring the fluid container 2 to the storing position 9, with the flat spring 23 contacting an upper side 24 of the fluid container 2 to secure the fluid container 2 against the container holder 10.

Stated more particularly, the flat springs 23 of all storing positions 9 of a same pipetting rack level 19 can be formed by a one-piece sheet 43, e.g. made of metallic material, such as, for example, steel, which, as illustrated in FIG. 1, enlarged detail view, can have spring cutouts 25 extending in y-direction in correspondence to the outer shape of the flat springs 23 having a common backward band 27 so that each flat spring 23 can be moved in z-direction relative to the other flat springs 23 with each flat spring 23 fixed to the backward band 27 so as to generate a resilient force. The backward band 27 extending in x-direction can be fixed to a housing side wall 4 by band fixation elements 29 such as, for example, screws. In one embodiment, the backward band 27 can be supported by a backing band 28 laid on and, e.g., fixed together with the backward band 27 so as to ensure that each flat spring 23 can generate a similar resilient force when bent upwards. Accordingly, each flat spring 23 can extend away from the housing side wall 4 to which the backward band 27 is fixed. Here, as e.g. illustrated in FIG. 4, in one embodiment, each flat spring 23 can have an upwardly bent (curved) shape to thereby form a contact portion 30 protruding towards and in direct contact with the upper side 24 of a fluid container 2 held in the storing position 9 by the container holder 10. The protruding contact portion 30 can be the only part of the flat spring 23 that can have contact with the fluid container 2. As a result, the fluid container 2 can reliably be kept in place by the biasing (resilient) force of the flat spring 23.

Figure 3:
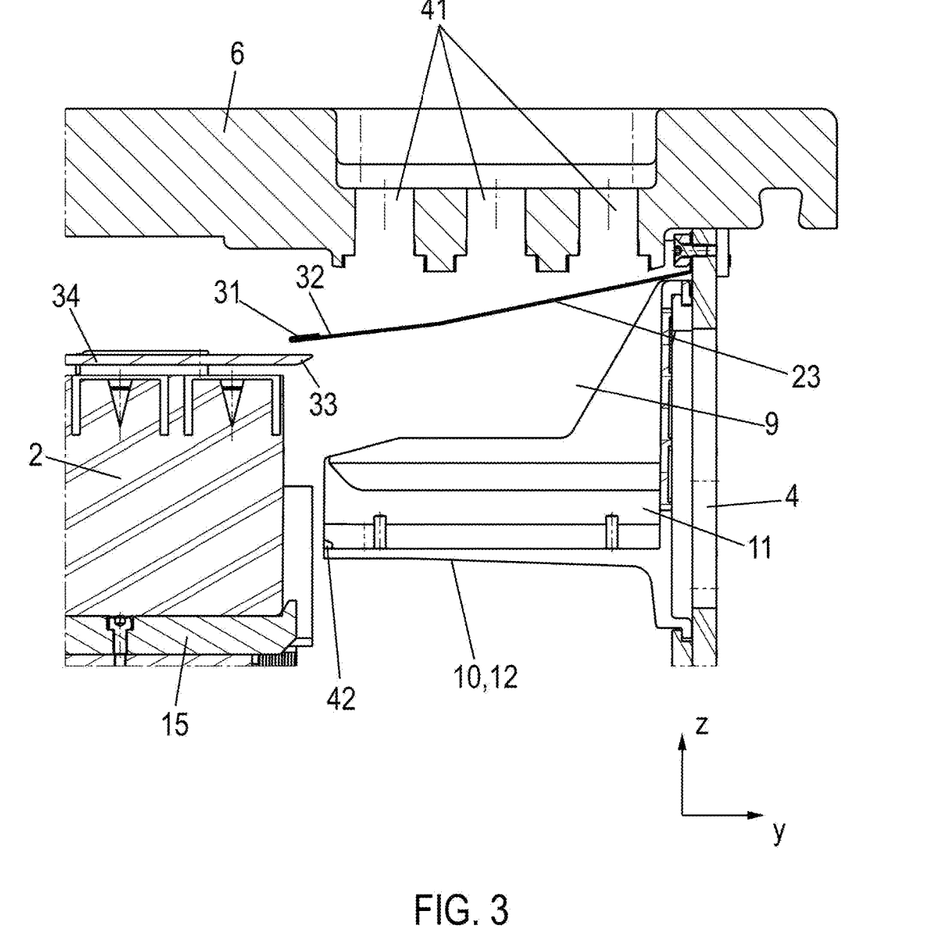
FIG. 3 illustrates an enlarged sectional view of a detail of the device of FIG. 1 according to an embodiment of the present disclosure.

With reference to FIG. 3, without contacting a fluid container 2, each flat spring 23 can be in a lowered state compared to a state in which the flat spring 23 contacts a fluid container 2. Stated another way, each flat spring 23 can be slightly lowered towards the container holder 10 below a level the upper side 24 of the fluid container 2 resides when the fluid container 2 can be inserted between the flat spring 23 and the container holder 10. As a result, by inserting the fluid container 2, elastic force acting on the upper side 24 of the fluid container 2 can be generated by the flat spring 23.

Figure 4:
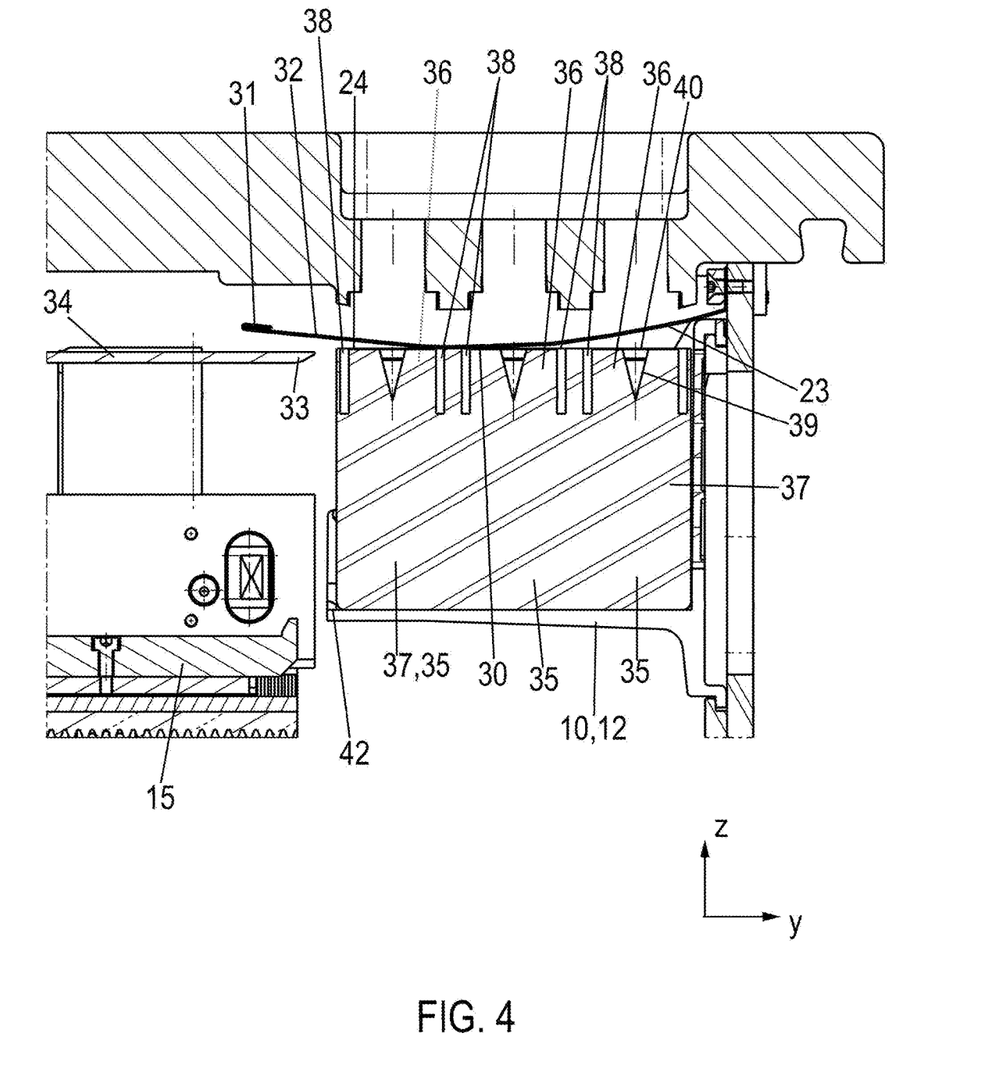
FIG. 4 illustrates a same view as FIG. 3 illustrating a storing position with a fluid container according to an embodiment of the present disclosure.
Figure 6:
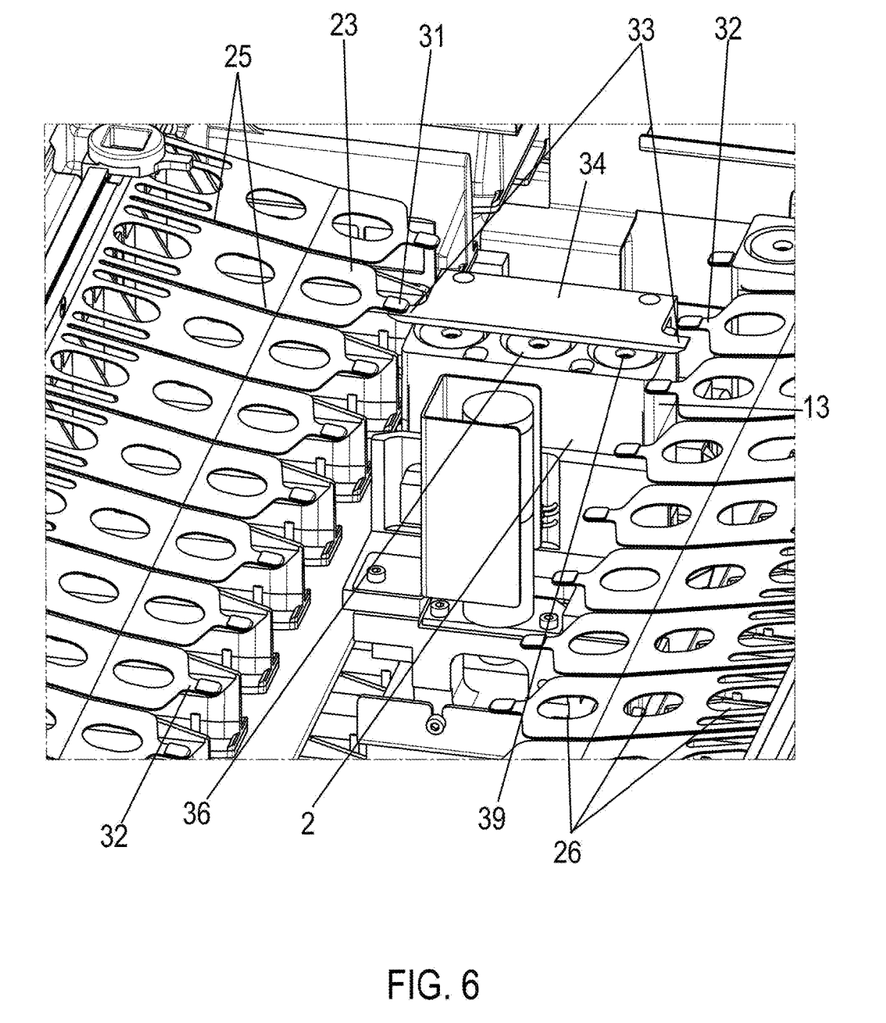
FIG. 6 illustrates a perspective view of an enlarged detail of the device of FIG. 1 illustrating engagement of the lug of the handler according to an embodiment of the present disclosure.
Figure 7:
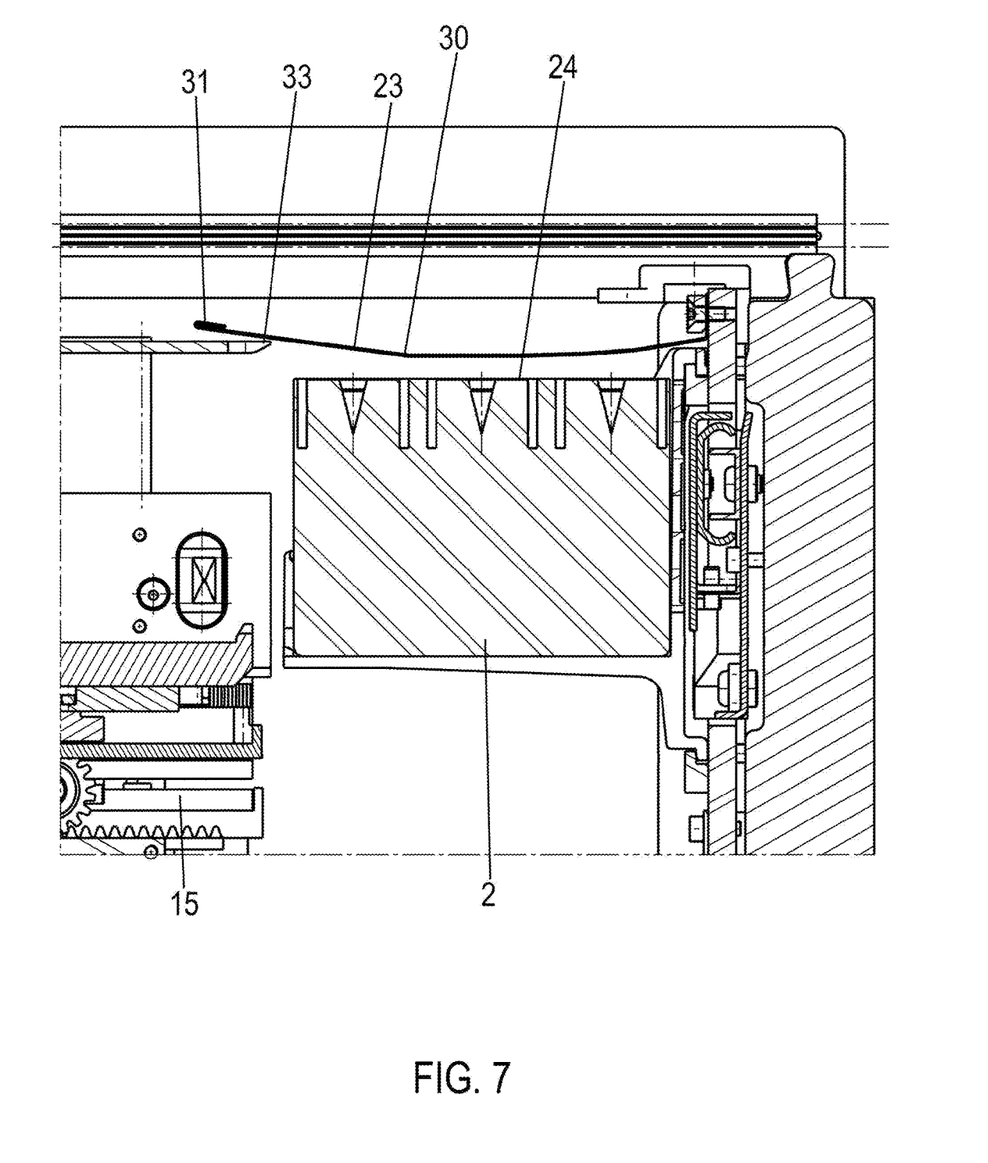
FIG. 7 illustrates an enlarged sectional view of a detail of the device of FIG. 1 illustrating engagement of the lug of the handler according to an embodiment of the present disclosure.

With continued reference to FIGS. 3 and 4 and further reference to FIG. 6, each flat spring 23 can have a nose 31 at a free-ending end portion 32 thereof. Each nose 31 can be brought in engagement with a lug 33 of the transfer head 15 of the handler 13. In one embodiment, the lug 33 can projects from a top portion 34 of the transfer head 15 towards the rack 7. In one embodiment illustrated in FIG. 6, each top portion 34 can have two lugs 33 facing the racks 7. Each lug 33 can be arranged in such a manner that the lug 33 can be in contact with the nose 31 of the flat spring 23 of a storing position 9 when the transfer head 15 is in transfer position relative to the storing position 9, i.e. faces the storing position so as to move a fluid container 2 towards or away from the storing position 9, in order to push the flat spring 23 upwards (in z-direction) against the resilient force so that the fluid container 2 can be moved relative to the storing position 9. Stated another way, in transfer position, the nose 31-contacting lug 33 can hold the flat spring 23 in a position which can be higher than the position of the flat spring 23 when there is no contact between the nose 31 and the lug 33 so that the flat spring 23 can lose contact to the upper side 24 of a fluid container 2 stored in the storing position 9.

Figure 5:
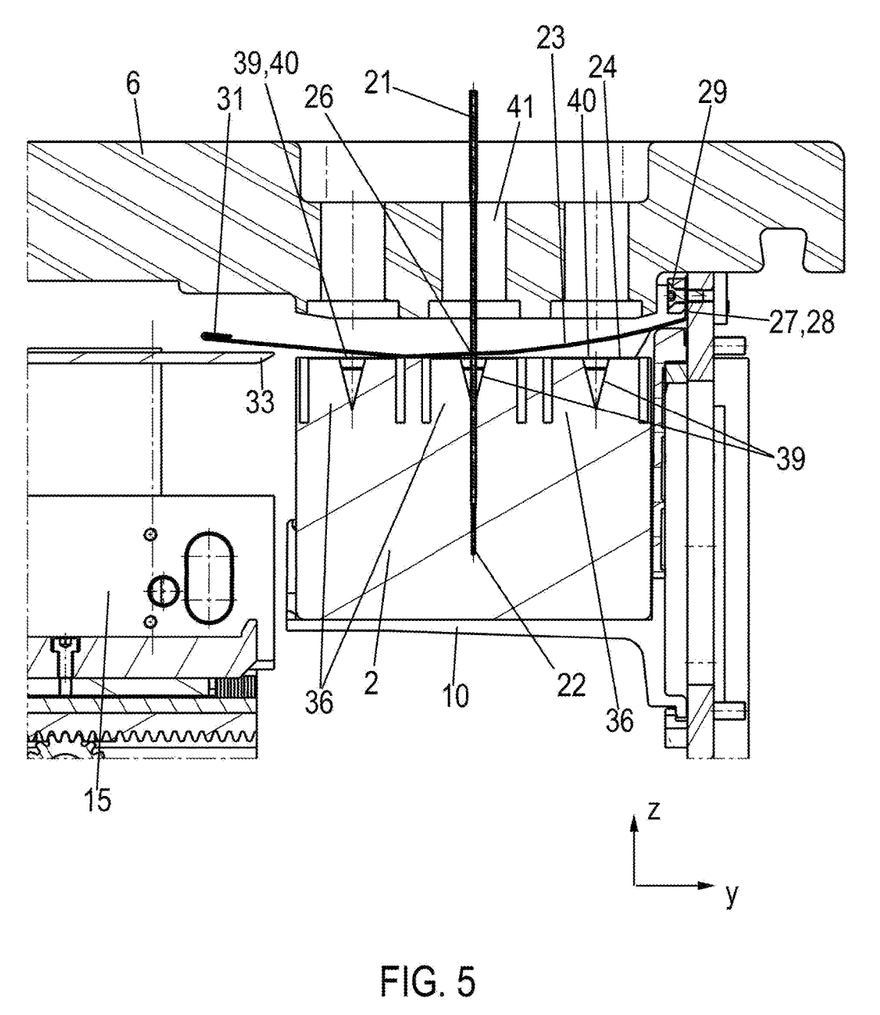
FIG. 5 illustrates a same view as FIG. 3 illustrating a storing position with a fluid container and a pipette penetrating the lid according to an embodiment of the present disclosure.

With particular reference to FIGS. 2 and 5, the system 100 can further include a pipettor 20 provided with one or more pipettes 21, each having a disposable pipette tip 22 or a re-usable pipette tip 22 such as, for example, a metallic needle, for transferring fluids to or from the fluid containers 2 stored in the pipetting rack level 19. Here, the pipettor 20 can be moved in a position right above a fluid container 2 in the pipetting rack level 19, with the one or more pipettes 21 movable towards or away from the fluid container 2.

With reference to FIG. 4, in one embodiment, each fluid container 2 can include a plurality of separate (fluid) compartments 35 serially arranged with respect to each other which may contain similar or different fluids, such as, for example, reagents in accordance with specific demands of the user. In one embodiment, each fluid container 2 can have three fluid compartments 35 that can be embodied as individual vials, bottles or the like. It, however, is to be understood that each fluid container 2 may include a larger or smaller number of fluid compartments 35 as desired. Each fluid compartment 35 can be provided with a lid 36 for closing an upper opening of the fluid compartment 35 which, e.g. can be screwed on the compartment body 37 or inserted in an opening 38 of the compartment body 37. When stored in a storing position 9, the plural fluid compartments 35 can be arranged in a row extending in y-direction.

With reference to FIGS. 2 and 5, each lid 36 can be configured to be punched through by the pipette tip 22 of a pipette 21. As illustrated in FIG. 5, in one embodiment, the lid 36 of each fluid compartment 35 can have a cone 39 arranged at and widening towards the upper side 24 so as to form a cone opening 40 at the upper side 24 of the fluid container 2 which can be punched through by a pipette tip 22. The cones 39 can, e.g., be made of plastic material. Furthermore, in one embodiment, a septum or membrane can be arranged at the cone opening 40. Accordingly, each fluid container 2 can have a plurality of cones 39, the number and arrangement of which can correspond to the number and arrangement of fluid compartments 35.

With reference to FIG. 1, in order to provide the pipettes 21 access to the fluid compartments 35, each flat spring 23 can have pipette cutouts 26, each configured as a hole in the flat spring 23. As illustrated, in one embodiment, the number and arrangement of pipette cutouts 26 of one flat spring 23 can correspond to a possible number and arrangement of lids 36 of a fluid container 2 stored in the associated storing position 9 of the pipetting rack level 19. Specifically, the pipette cutouts 26 can be serially arranged with respect to each other in a row extending in the y-direction. In one embodiment, each pipette cutout 26 can have a round shape. In one embodiment, each pipette cutout 26 can have a slightly oval shape. Furthermore, with reference to FIG. 3, in order to provide the pipettes 21 access to the fluid compartments 35, the housing top wall 6 can be provided with wall holes 41. In one embodiment, the number and arrangement of wall holes 41 can correspond to a possible number and arrangement of lids 36 of a fluid container 2 stored in the storing positions 9 of each pipetting rack level 19. Specifically, the wall holes 41 associated with one storing position 9 can be serially arranged with respect to each other in a row extending in the y-direction. In one embodiment, each wall hole 41 can have a rounded shape.

Accordingly, in the system 100, at least one pipette 21 can be lowered towards a lid 36 of a fluid compartment 35 of a fluid container 2 in a storing position 9 of the pipetting rack level 19 of a rack 7, with the pipette tip 22 being moved both through a wall hole 41 of the housing top wall 6 and through a pipette cutout 26 of a flat spring 23. By continuing lowering, the pipette tip 22 can penetrate the penetrable lid 36 of the fluid compartment 35 so as to dip the pipette tip 22 into fluid contained therein in order to suck-in the fluid. In one embodiment, due to having wall holes 41 both in correspondence to the pipette cutouts 26 of the flat springs 23 (corresponding to the number and arrangement of lids 36 of a fluid container 2 stored in the associated storing position 9), access to any fluid compartment 35 by one or more pipettes 21 may occur at any time. Also, it can be possible that a number of pipettes 21 (e.g. three) corresponding to the number of lids 36 (e.g. three) of a fluid container 2 stored in the storing position 9 can be lowered towards the fluid container 2 so as to simultaneously pipette fluids with respect to the fluid compartments 35 of the fluid container 2.

When pulling the one or more pipettes 21 out of the fluid container 2 in the storing position 9 of the pipetting rack level 19, a frictional force can usually arise between the pipettes 21 and the fluid container 2. In the case of using several pipettes 21 for simultaneously pipetting fluids of one fluid container 2, the frictional force can increase according to the number of pipettes 21. Due to the resilient force of the flat spring 23 acting on the fluid container 2 counteracting the frictional force, the fluid container 2 cannot be moved in z-direction and thus kept in place. As a result, further pipetting operations can be reliably performed without a risk of a crash between the fluid container 2 and pipettes 21.

As e.g. illustrated in FIG. 1, in one embodiment, the container holder 10 can comprise a holder projection 42 at the end portions of each holder bottom plate 12 which can be brought in fitting engagement with a fluid container 2 so as to block movement of the fluid container 2 relative to a transfer direction for transferring the fluid container 2 to or away from the storing position 9 by using the handler 13. Accordingly, the fluid container 2 can be secured by the container holder 10 relative to the transfer direction. As a result, together with the resilient force of the flat spring 23 pressing the fluid container 2 against the container holder 10, fixation of the fluid container 2 can be improved.

In one embodiment, the system 100 can further include a controller for controlling the handling of fluid containers 2 by the handler 13. The controller may, e.g., be embodied as a programmable logic controller running a machine-readable program provided with instructions to perform operations in accordance with a predetermined process operation plan. In that, the controller can be electrically connected to the system components which require control, so that the controller can be enabled to receive information from the different system components and to transmit corresponding control signals for controlling the components according to the process operation plan, particularly including the handler 13 for transferring fluid containers 2 with respect to the storing positions 9 as well as an input-/output position.

As detailed above, in the system 100, fluid containers 2 can be transferred in and with respect to the storing positions 9. Specifically, fluid containers 2 can be transferred with respect to the storing positions 9 of a same rack level 8 and/or can also be transferred between different rack levels 8 by the handler 13. In particular, fluid containers 2 can be transferred to the uppermost pipetting rack level 19 of each rack 7 so as to provide the pipettes 21 free access to the fluid containers 2 through the housing top wall 6 and the flat springs 23. Accordingly, there may not be a need to remove fluid containers 2 from the device 1 to perform pipetting operations. Specifically, as a result, the fluid containers 2 can be efficiently cooled before, after and even during pipetting operations. Furthermore, a separate step of opening fluid containers 2 can be avoided by using a pipette tip 22 capable of punching through the lids 36 of the fluid containers 2. Due to the resilient force of the flat springs 23 counteracting the frictional force arising when the pipettes 21 are pulled out of the fluid containers 2, upwards movements of the fluid containers 2 can be avoided.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A device for storing of fluid containers, the device comprising:
    at least one storage provided with a plurality of storing levels including a pipetting storing level adapted for pipetting of fluids, each storing level having a plurality of storing positions, each of which having a container holder adapted to detachably hold at least one fluid container; and
    a handler movable with respect to the storage adapted for automatically transferring fluid containers at least with respect to the storing positions, wherein a storing position of the pipetting storing level includes a flat spring arranged to bias a fluid container against the container holder by forcing the fluid container against the container holder by a resilient force generated by the flat spring onto the fluid container, with the flat spring provided with at least one through-hole positioned to provide a pipette access to a container lid of the fluid container, wherein the handler comprises a lug and wherein when the lug contacts the flat spring, the lug holds the flat spring in a position above a position of the flat spring without contact between the lug and the flat spring so that the flat spring no longer contacts the fluid container and no longer generates the resilient force onto the fluid container.

2. The device according to claim 1, further comprising, a device housing, wherein the at least one through-hole of the flat spring is positioned to align with a hole of the device housing to provide access for a pipette to a container lid of the fluid container from outside the device housing.

3. The device according to claim 1, wherein the lug is configured to be engaged with the flat spring of a storing position so as to act against the resilient force of the flat spring when the handler is in a transfer position for transferring a fluid container to or away from the storing position.

4. The device according to claim 3, wherein the flat spring has a curved shape so as to have at least one contact portion for contacting a fluid container in a storing position with the contact portion protruding towards the fluid container.

5. The device according to claim 3, wherein a free-ending end portion of the flat spring protrudes from the storing position for engagement with the lug of the handler.

6. The device according to claim 1, wherein the container holder of a storing position comprises a projection configured to be brought in fitting engagement with a fluid container held by the container holder so as to block movement of the fluid container relative to a transfer direction for transferring the fluid container to or away from the storing position.

7. The device according to claim 1, wherein each storing level extends in a plane (X, Y).

8. The device according to claim 7, wherein the plurality of storing levels are stacked in a direction (Z) orthogonally aligned to the plane (X, Y), with the pipetting storing level being an upper storing level.

9. The device according to claim 1, wherein the flat spring comprises one or more through-holes positioned to provide one or more pipettes access to a corresponding number of penetrable lids of a fluid container.

10. The device according to claim 1, wherein a plurality of flat springs are formed from a one-piece sheet.

11. A system for pipetting of fluids, the system comprising:
    at least one device according to claim 1; and
    a pipettor movable at least with respect to the pipetting storing level provided with at least one pipette for pipetting of fluid contained in a fluid container stored in the pipetting storing level, wherein the pipette has a pipette tip configured to penetrate a lid of the fluid container.

12. The system according to claim 11, wherein the device according to claim 1 is a modular system component.

* * * * *